United States Patent [19]

Takamatsu

[11] Patent Number: 4,504,686

[45] Date of Patent: Mar. 12, 1985

[54] PROCESS FOR PREPARING 1,1,2-TRIFLUORO-2-CHLOROETHYL DIFLUOROMETHYL ETHER

[75] Inventor: Shuichi Takamatsu, Kawanishi, Japan

[73] Assignee: Daikin Kogyo Co., Ltd., Osaka, Japan

[21] Appl. No.: 636,786

[22] Filed: Aug. 1, 1984

Related U.S. Application Data

[63] Continuation of Ser. No. 408,231, Aug. 16, 1982, abandoned.

[51] Int. Cl.$^3$ ............................................. C07C 41/22
[52] U.S. Cl. .................................................. 568/684
[58] Field of Search ................................ 568/684, 683

[56] References Cited

U.S. PATENT DOCUMENTS 3,469,011 9/1969 Terrell .
4,088,701 5/1978 Siegemund et al. .

Primary Examiner—Howard T. Mars
Attorney, Agent, or Firm—Birch, Stewart, Kolasch & Birch

[57] ABSTRACT 1,1,2-Trifluoro-2-chloroethyl difluoromethyl ether is prepared in a good yield by reacting 1,1,2-trifluoro-2-chloroethyl dichloromethyl ether with hydrogen fluoride at a gaseous phase.

4 Claims, No Drawings

PROCESS FOR PREPARING 1,1,2-TRIFLUORO-2-CHLOROETHYL DIFLUOROMETHYL ETHER

This application is a continuation of application Ser. No. 408,231 filed on Aug. 16, 1982, now abandoned.

The present invention relates to a process for preparing 1,1,2-trifluoro-2-chloroethyl difluoromethyl ether. More particularly, it relates to an improved process for preparing 1,1,2-trifluoro-2-chloroethyl difluoromethyl ether by reacting 1,1,2-trifluoro-2-chloroethyl dichloromethyl ether with hydrogen fluoride.

1,1,2-Trifluoro-2-chloroethyl difluoromethyl ether, useful as an anesthetic, has been prepared by fluorinating 1,1,2-trifluoro-2-chloroethyl dichloromethyl ether with hydrogen fluoride in a liquid phase in the presence of an antimony (V) catalyst or a tin (IV) catalyst (cf. Japanese Patent Publication (unexamined) No. 3,606/1973). However, this process is disadvantageous in that it is difficult to carry out the reaction continuously. It is also disadvantageous in that the catalyst, after completion of the reaction, must be decomposed with water and removed.

As a result of extensive study, it has been found that 1,1,2-trifluoro-2-chloroethyl difluoromethyl ether can be prepared at a good yield by reacting in a gaseous phase 1,1,2-trifluoro-2-chloroethyl dichloromethyl ether with hydrogen fluoride.

Accordingly, the present invention provides a process for preparing 1,1,2-trifluoro-2-chloroethyl difluoromethyl ether which comprises reacting 1,1,2-trifluoro-2-chloroethyl dichloromethyl ether with hydrogen fluoride in a gaseous phase.

In the above conventional liquid-phase fluorination process, a use of the catalyst is essential for the rate of the reaction to be practical. Further, the fluorination is preferably carried out at a temperature of from 0° C. to 10° C. At a higher temperature, a side reaction may proceed. To the contrary, the gas phase fluorination according to the present invention can well proceed in the absence of a catalyst, but proceeds more advantageously in the presence of a catalyst. Further, the fluorination may be carried out not only at a low temperature but also at a higher temperature with a good yield.

The fluorination of the invention can be carried out continuously with a high yield. When a catalyst is used, continuous operation is possible over a long period of time without wasting the catalyst. These make the process of the invention advantageous in the industry.

As stated above, the fluorination of the present invention may be carried out in the presence or absence of a catalyst, and the desired fluorinated product is obtainable at a good yield. Practically and usually, the catalyst is used, whereby the reaction is accelerated.

The catalyst may be any one conventionally employed for fluorination; specific examples are oxyfluorides of molybdenum, fluorides and oxyfluorides of chromium, thallium, aluminum, etc. These may be used as such or deposited on a carrier, such as activated charcoal, alumina, fluorinated alumina, calcium fluoride, sodium fluoride and magnesium fluoride. Strong Lewis acids such as titanium tetrafluoride are not favorable, because a clear tendency to lower the yield is observed.

The reaction temperature is usually from the boiling point of 1,1,2-trifluoro-2-chloroethyl dichloromethyl ether (about 115° C. at atmospheric pressure) to 400° C., particularly from 200° C. to 400° C. when the catalyst is not used, and from the boiling point to 350° C. when the catalyst is used. At too high a reaction temperature, the ether linkage is broken to lower the yield. Thus, the reaction temperature is preferred to be as low as possible in the stated range.

The reaction pressure is not critical and preferably from 0.5 to 10 atm.

The molar ratio of the starting ether and hydrogen fluoride is not critical and may be usually from 1:2 to 1:20. The space velocity is also not critical and may be usually from 10 to 10,000 hr$^{-1}$. When, for example, 1,1,2-trifluoro-2-chloroethyl dichloromethyl ether and hydrogen fluoride are reacted in a molar ratio of 1:16 in the absence of the catalyst at 20° C. with a space velocity of 30 hr$^{-1}$, the yield is 69.6%. When the same starting materials as above are reacted in the same molar ratio as above in the presence of $MoO_xF_y$ deposited on activated charcoal at 160° C. with a space velocity of 474 hr$^{-1}$, the yield is 92.1%.

In the fluorination of the invention, the reaction may proceed according to the following reaction formula:

$$CHCl_2OCF_2CFClH \rightarrow$$

$$CHClFOCF_2CFClH \rightarrow$$

$$CHF_2OCF_2CFClH$$

Therefore, an intermediate 1,1,2-trifluoro-2-chloroethyl chlorofluoromethyl ether may be contained in the resulting reaction mixture and can easily be recovered on separation of the desired product 1,1,2-trifluoro-2-chloroethyl difluoromethyl ether from the reaction mixture by distillation. The recovered intermediate may be further fluorinated to produce the desired product, which improves the yield.

The present invention will be hereinafter explained in detail by the following Examples.

EXAMPLE 1

Molybdenum trioxide (5.5 g) was dissolved in 28% aqueous ammonia (50 g) by heating. To the resulting solution, activated charcoal (43 g, about 100 ml) was added, and then water and ammonia were evaporated off under reduced pressure. The residue was charged into the middle portion of a reaction tube made of Hastelloy C (trade name) having an inner diameter of 1 inch, which was placed in an electric furnace, heated in a stream of nitrogen at 300° C. for about 5 hours to remove water and ammonia completely and then treated with anhydrous hydrogen fluoride at 300° C. for about 5 hours to produce a $MoO_xF_y$ catalyst.

1,1,2-Trifluoro-2-chloroethyl dichloromethyl ether and anhydrous hydrogen fluoride in a molar ratio of 1:16 were passed through in a preheating mixing tube and then the bed of the catalyst in the reaction tube kept at 160° C. with a space velocity of 474 hr$^{-1}$. The gaseous reaction mixture was passed through ice water and trapped with a dry-ice/acetone cooled trap. Gas chromatographic analysis of the trapped reaction mixture showed that the yields of 1,1,2-trifluoro-2-chloroethyl difluoromethyl ether, of 1,1,2-trifluoro-2-chloroethyl chlorofluoromethyl ether and of 1,1,2-trifluoro-2-chloroethyl dichloromethyl ether were respectively 92.1%, 1.8% and 0.2%.

EXAMPLES 2 TO 6

In the same manner as in Example 1 but using the catalyst, the space velocity and the reaction temperature as shown in table 1, the reaction was carried out. Among the catalysts, $MoO_xF_y$/activated charcoal was the same as prepared in Example 1; —$AlF_3$ was a commercial available one; and $CrO_xF_y$ and $TlO_xF_y$ were prepared by treating $Cr_2O_3$ or $CrO_3$ and $Tl_2O_3$ with anhydrous hydrogen fluoride for several hours at a temperature of from 200° C. to 450° C. and of 150° C., respectively.

TABLE 1

| Example | Catalyst | Space velocity (hr$^{-1}$) | Reaction temperature (°C.) | Yield (%) A*1 | B*2 | C*3 |
| --- | --- | --- | --- | --- | --- | --- |
| 2 | $MoO_xF_y$/Activated Charcoal | 474 | 210 | 90.2 | 2.1 | 0.3 |
| 3 | $CrO_xF_y$ | 474 | 125 | 82.2 | 2.4 | 0.2 |
| 4 | α-$AlF_3$ | 474 | 220 | 26.4 | 38.4 | 14.0 |
| 5 | — | 31 | 245 | 69.6 | 7.3 | 0.4 |
| 6 | $TlO_xF_y$ | 474 | 150 | 78.6 | 5.2 | 5.5 |

Note:
*1 1,1,2-Trifluoro-2-chloroethyl difluoromethyl ether
*2 1,1,2-Trifluoro-2-chloroethyl chlorofluoromethyl ether
*3 1,1,2-Trifluoro-2-chloroethyl dichloromethyl ether

What is claimed is:

1. A process for preparing 1,1,2-trifluoro-2-chloroethyl difluoromethyl ether which comprises reacting 1,1,2-trifluoro-2-chloroethyl dichloromethyl ether with hydrogen fluoride in a gaseous phase in the absence of a catalyst or in the presence of a catalyst selected from the group consisting of oxyfluorides of molybdenum, fluorides and oxyfluorides of chromium, thallium and aluminum.

2. The process according to claim 1, wherein the reaction is carried out at a temperature of from the boiling point of the starting ether to 400° C.

3. The process according to claim 1, wherein the reaction is carried out at a temperature of from 200° C. to 400° C. in the absence of a catalyst.

4. The process according to claim 1, wherein the reaction is carried out at a temperature of from the boiling point of the starting ether to 350° C. in the presence of said catalyst.

* * * * *